(12) United States Patent
Karapetyan (10) Patent No.: US 8,814,565 B1
(45) Date of Patent: Aug. 26, 2014

(54) SURGICAL DEVICE FOR DENTAL IMPLANT INSTALLATION

(76) Inventor: Armen Karapetyan, Los Angeles, CA (US)

( * ) Notice: Subject to any disclaimer, the term of this patent is extended or adjusted under 35 U.S.C. 154(b) by 173 days.

(21) Appl. No.: 13/373,593

(22) Filed: Nov. 21, 2011

(51) Int. Cl.
*A61C 3/00* (2006.01)

(52) U.S. Cl.
USPC .......................................................... 433/75

(58) Field of Classification Search
USPC ......... 433/25, 72, 74, 75, 141, 146, 153, 157, 433/158, 215; 33/501, 511–514; 606/86, 606/96, 99, 102
See application file for complete search history.

(56) References Cited

U.S. PATENT DOCUMENTS

| | | | | |
|---|---|---|---|---|
| 5,711,315 A | * | 1/1998 | Jerusalmy | ...................... 128/898 |
| 5,989,025 A | * | 11/1999 | Conley | ............................ 433/76 |
| 7,125,253 B2 | * | 10/2006 | Kitamura et al. | ............. 433/173 |
| 7,662,188 B2 | | 2/2010 | Yamada | |
| 7,771,199 B2 | | 8/2010 | Hochman et al. | |
| 7,837,707 B2 | * | 11/2010 | Yamada | ......................... 606/213 |
| 8,029,284 B2 | | 10/2011 | Better et al. | |
| 8,029,523 B2 | | 10/2011 | Wallis et al. | |
| 2001/0012607 A1 | | 8/2001 | Robinson | |
| 2006/0264828 A1 | * | 11/2006 | Woehr et al. | ................... 604/110 |
| 2008/0161846 A1 | * | 7/2008 | Yamada | ......................... 606/190 |
| 2008/0161934 A1 | * | 7/2008 | Yamada | ..................... 623/17.17 |
| 2010/0221681 A1 | * | 9/2010 | Hochman | ...................... 433/173 |
| 2010/0255444 A1 | * | 10/2010 | Karmon | ......................... 433/172 |

* cited by examiner

*Primary Examiner* — Cris L Rodriguez
*Assistant Examiner* — Justin O'Donnell (57) ABSTRACT

This invention provides the safe elevation of the Schneiderian membrane for the tissue regeneration especially bone augmentation for dental implant before surgical placement of the dental implants in the grown maxillary jaw bone in order to obtain adequate volume of osseous structure by addition of the artificial bone draft material. A surgical device can include a main portion, a handle portion, a main element, an adjustment mechanism, an adjustment portion, an outer thread, a free end, a depth measurement marks, the first and second connection sections, a cylinder, the inner and outer threads, the first and second projections, and a handle element with a texture.

1 Claim, 5 Drawing Sheets fig. 1

VIEW 34-34

SURGICAL DEVICE FOR DENTAL IMPLANT INSTALLATION

BACKGROUND OF THE INVENTION

1. Field of the Invention

The invention relates to the dental surgical devices for elevating the Schneiderian membrane, and more particularly, to the dental devices for bone augmentation for dental implant. Specifically, the invention relates to the devices which are designed for the surgical placement of the dental implants in the maxillary jaw bone. Still more specifically, this invention relates to the growing of jaw bone in order to obtain adequate volume of osseous structure for dental implant.

2. Description of Related Art

Due to the destructive nature of dentures to the underlying jaw bone as well as to the fact that bone that is not internally stimulated by tooth roots will atrophy, the amount of bone in many people is very limited for the placement of dental implants. The successful placement of the dental implants is very well known and is based on a variety of factors including: surgical technique, health of the patient, operator skill and, to a significant part, sufficient bone for the placement and integration of the dental implant. The dental implants are generally used in the anterior lower jaw, as this region provides sufficient bone quantity, quality and strength to support and hold the installed dental implant. However, the replacement of the maxillary teeth have presented a considerable challenge because after the loss of maxillary teeth the quality and quantity of the remaining supporting bone may be insufficient to properly and reliably support the dental implant. Also, the success of the dental implants has been limited by the quality and quantity of existing bone a given patient would present with. For example, individual tooth implants have been successfully carried out, and this procedure is now relatively common, but again, this process may not be suitable for many dental patients due to a lack of available bone.

It is known that the maxillary bone structure composed of alveolar bone and basal bone. The maxillary teeth, and more specifically the teeth roots, are located in the alveolar bone. The upper surface of the maxillary structure is the floor of the maxillary sinus and is in contact with a thin Schneiderian membrane (also known as "subantral membrane" or "sinus membrane" [hereinafter may be mentioned as "membrane"]). After tooth is removed from the maxillary bone, the surrounding alveolar bone is frequently resorbed because of the lack of physical stimulation and support of the teeth. This, as it is well known, leads to a loss of bone mass and a corresponding reduction in the effective height and thickness of the bone of the maxillary complex, which if not restored would limit the potential use of the dental implant. In order to overcome the deficiency of insufficient vertical bone mass of the maxillary complex, There are known in the dentistry some surgical techniques to increase the bone mass for the placement of dental implants. These techniques augment the bone deficient region with a regenerative synthetic graft material, which should be placed between the upper surface of the maxillary bone and membrane in such manner that it does not traumatize or even injure the membrane and does not interfere with the function of the maxillary sinus. Thus, the membrane should be carefully lifted to provide some space for the artificial bone draft material without osteogenesis distraction.

If the membrane is not carefully and properly lifted, the bone augmentation process may puncture the thin sinus membrane creating serious medical consequences.

The one of the membrane lifting procedure is known as Dr. R. B. Summers' procedure, providing the approach to the maxillary sinus from the alveolar ridge utilizing solid cylindrical instrument. The instrument vertically mechanically lifts the membrane from the bottom area of the maxillary sinus. The graft material is then placed into the freed space between the elevated membrane and upper surface of the maxillary bone through the aperture in the bone (e.g., trough the socket of the extracted tooth, etc.). The dentist should be very careful and precise moving the instrument through the socket in order not to tear, ripping or perforate the membrane by pushing the instrument in the sinus compartment far away from the line of the upper surface of the maxillary bone, considering the missing feedback.

The one of the known techniques for dental implant installation in the maxillary jaw uses the sleeve inserted through the alveolar ridge to the maxillary sinus. The sleeve is used to raise the Schneiderian membrane and form a cavity. A bone growth stimulant (draft material), is injected through the sleeve into the cavity. In the process, the sleeve also can cut and/or condense the bone around itself so that the bone can hold an implant. Optionally, the bone draft material is also introduced into the bone surrounding the sleeve. During the injection, the pressure within the sleeve or the cavity is monitored to detect and prevent the rupture of the membrane.

Such device(s) are very complex and do not provide sufficient safety for membrane.

The Patent Application Publication No. US2001/0012607 describes a method of growing additional maxillary (or mandibular) bone in areas of atrophy and by the use of a related device to accomplish the task. A pliable guided-tissue regeneration plate, which holds it shape after being bent, is employed as a mating component to a support screw or a dental implant and is secured to the jaw structure by fixation of the guided-tissue regeneration plate at a predetermined distance above or away from the surface of the bone to the support screw or dental implant in order to create a supported and protected space between the underside of the gum tissue and the original bone which is free from muscular and chewing pressure in order to promote bone growth.

The guided-tissue regeneration plate support and fixation system can be mated with a support screw or screws which are tenting screws designed to be mated with and then become intimately a part of the guided-tissue regeneration plate in order to grow bone in the space created by the guided-tissue regeneration plate system prior to implant placement. Additionally, the guided-tissue regeneration plate system can be utilized during implant placement by creating space adjacent to a dehisced implant by fixation of the guided-tissue regeneration plate directly to the implant in order to grow bone height or width. A guided-tissue regeneration plate according to the present invention can also be used by affixing it to an existing dental implant that has been previously placed and has undergone bone loss in order to regenerate new bone. The guided-tissue regeneration plate support and fixation system is adapted to be surgically removed after the bone has grown under its surface at a later uncovering or implant placement surgery. In an alternative preferred embodiment which provides particularly successful results and which results in faster and better bone regeneration and periosteum growth, the guided-tissue regeneration plate consists of first and second integrated components including a first support plate component having a peripheral region and a generally open central portion and a fine mesh screen juxtaposed over the central portion and fixed to the peripheral region thereof. In a functionally equivalent variant of the alternative preferred embodiment, the guided-tissue regeneration plate is fabricated starting with an imperforate plate (for example, of titanium) and then reducing the thickness of predetermined central regions of the plate, a step which can be carried out, for example, by employing a conventional photoresist mask over the plate in conjunction with an acid etch. After the desired thickness of the central regions has been obtained, the central regions may be perforated with finely spaced apertures using, for example, conventional laser machining techniques.

Specifically, the invention uses guided-tissue regeneration plate which has been molded, then bone graft material is packed beneath the plate and against the existing bony ridge. After a period of approximately four-to-eight months, a new bony ridge will form within the space created by the guided-tissue regeneration plate support, its fixation system, and the cortical bone (more precisely, the gum tissue). In order to place a guided-tissue regeneration plate support and fixation system according to the present invention, the tissue is first reflected away from the bony ridge to expose the ridge in its entirety. The palatal gum tissue is reflected, the facial gum tissue is reflected, and a guided-tissue regeneration plate support screw is placed into the bony ridge. Later the guided-tissue regeneration plate support and fixation system has been removed exposing the new bony ridge (a small hole remains after the removal of the guided-tissue regeneration plate support screw) and implant can be placed (installed) into the new bony ridge (a tooth can be attached to the implant later).

Such method may easily traumatize the tissue.

Another known techniques for dental implant installation in the maxillary jaw utilizes a surgical tool used for preparing a surgical sinus-lift. The tool has an instrumental tip to cut, crack and push bone from the sinus floor upward into the sinus. The apical instrumental tip is driven into a pre-drilled pilot after the cutting maxillary bone threads are engaged and rotated until the sinus floor is cracked free. Once the bony sinus floor is cracked free, a fluid passageway can be pressurized with a sterile fluid at a defined pressure to release and push the sinus membrane upward into the sinus cavity to create a desired apical cavity for grafting.

For instance, the devices by U.S. Pat. Nos. 7,771,199 and 8,029,284 use the fluid pressure to release and push the sinus membrane:

a) the U.S. Pat. No. 7,771,199 to Hochman et al. comprises the defined thread geometry in series with an instrumental tip to cut, crack and push bone from the sinus floor upward into the sinus cavity in a tactual, gentle and controlled motion. The apical instrumental tip is driven into a pre-drilled pilot after the cutting threads are engaged and rotated until the sinus floor is cracked free. Once the bony sinus floor is cracked free, a fluid passageway can be pressurized with a sterile fluid at a defined pressure to release and push the sinus membrane upward into the sinus cavity to create a desired apical cavity for grafting while minimizing the risk of compromising or tearing the sinus membrane.

b) the U.S. Pat. No. 8,029,284 to Better et al. includes a dental implant having a proximal implant end and a lateral external surface. The implant is shaped so as to define a lumen therethrough having a lateral opening through the lateral external surface. The apparatus further includes an applicator, which is removably coupled to the proximal implant end. The applicator includes a delivery tube having a distal tube end that is removably coupled to the implant such that the delivery tube is in fluid communication with the lumen via the lateral opening. Other embodiments are also described.

Another device by U.S. Pat. No. 8,029,523 to Willis et al. includes a tubular element, and a cutter spring-biased relative to the tubular element. In an unloaded configuration the cutter is displaced relative to the tubular element by a displacement distance, and when the cutter is in a loaded configuration the displacement distance is reduced. A first structure is longitudinally fixed relative to the cutter and rotationally engaged relative to the tubular element. A length of the first structure extends proximally in the unloaded configuration. A second structure is longitudinally displaceable relative to the first structure. In the loaded configuration, a driver engages and rotates both the first and second structures, and thus the tubular element and cutter together. Once the cutter breaks through the bone, the cutter spring-biased into the unloaded configuration, resulting in disengagement of the first structure from the driver to prevent rotation of either the tubular element or the cutter. When the main cutter has pierced all maxillary bone, the spring causes the auxiliary cutter to lift the membrane.

Some techniques describes an implant comprising at least one shaft area for anchoring in a bony structure, and at least one opening at the distal end of the shaft area in which the shaft area has a continuous bore extending from the opening to at least one outlet at the apical end, so that targeted introduction of material at least into the periapical area is possible with a stable anchoring in the bone structure even after implantation.

The U.S. Pat. No. 7,662,188 to Yamada discloses an internal sinus manipulation procedure and instrument for augmenting bone of a dental patient between the floor of the patient's sinus and a raised portion of the patient's sinus membrane comprising exposing a portion of the patient's sinus membrane immediately adjacent the floor of the patient's sinus followed by a lifting and lateral separation of the exposed portion of the sinus membrane from the sinus floor to form an open pocket between the sinus membrane and the sinus floor.

Specifically, following the formation of the bone aperture (channel), a conventional depth gauge instrument having axially spaced measuring marks and a blunt tip is employed to measure the thickness of the bone in the channel and to verify the amount of the membrane lifting previously determined in the development of the patient treatment plan.

All these devices have a deficiency—they depend only on carefulness of the dentist with respect to the membrane elevation. They do not provide a limitation of the deepness of the passage through the jaw's aperture into sinus compartment, thereby, creating dangerous lifting of the Schneiderian membrane considering possible sudden, unexpectedly stressed movements of the dentist's hands during membrane elevation, etc.

Therefore, the mentioned known methods and devices have the described above deficiencies which are eliminated in the improved surgical device for elevating the Schneiderian membrane.

While the mentioned above prior art fulfill their respective, particular objectives and requirements, the mentioned inventions do not disclose, teach and/or suggest the device for dental implant installation including the elements (components/parts) inflating its/their capacity/volume to securely move the Schneiderian membrane providing internal place for the material drafting the artificial bone(s).

Those skilled in the art will readily observe that numerous modifications and advantages of the improved device for dental implant installation may be made while retaining the teachings of the invention.

Thus, the known prior art do not provide the efficient, satisfied, convenient device for dental implant installation according to the present invention substantially departs from the devices of the prior art.

Accordingly, several objects and advantages of the present invention are to provide the improved surgical device for elevating the Schneiderian membrane:

It is another object of the invention increase the safety of the Schneiderian membrane during dental procedure of elevation the Schneiderian membrane.

It is further object of the invention to minimize the possible traumatization of the Schneiderian membrane during lifting of the Schneiderian membrane.

It is still another object of the invention to increase the convenience and efficiency of the dental device for preparation of the dental implant installation.

BRIEF SUMMARY OF THE INVENTION

In view of the foregoing disadvantages inherent in the known prior art, the present invention provides an improved surgical device for elevating the Schneiderian membrane. As such, the general purpose of the present invention, which will be described hereinafter in greater details, is to provide the device for dental implant installation, which has many of the advantages of the dental implant installation mentioned heretofore and many novel features that result in the safety procedure with the Schneiderian membrane, which is not anticipated, rendered obvious, suggested or even implied by any of prior art methods and dental devices, either alone or in any combination thereof.

To attain this, the present invention generally comprises the surgical device for the dental implant installation. An improved surgical device for elevating the Schneiderian membrane includes a main portion, a handle portion, which comprise a main means, an adjustment means, an adjustment portion, an outer thread, a free end, a depth measurement marks, the first and second connection sections, a cylinder, the inner and outer threads, the first and second projections, and a handle means with a texture.

BRIEF DESCRIPTION OF THE DRAWINGS

In order that the invention and the manner in which it is to be performed may be more clearly understood, embodiments thereof will be described by way of example with reference to the attached drawings, of which.

THE DRAWING REFERENCE NUMERALS

1.—a main portion;
2.—a handle portion;
3.—a main means;
4.—an adjustment means;
5.—an adjustment portion;
6.—an outer thread;
7.—a free end;
8.—a depth measurement marks;
9.—a first connection section;
10.—a cylinder;
11.—an inner thread;
12.—a handle means;
13.—a second connection section;
14.—a texture;
15.—a Schneiderian membrane;
16.—a tooth socket;
17.—a lower surface of the gum 18;
18.—a gum;
19.—an upper surface of the jaw bone 20;
20.—a jaw bone;
21.—a sinus compartment;
22.—a first projection;
23.—a second projection;
24.—a top of the first projection 22;
25.—a top of the second projection 23;
26.—a draft material pocket;
27.—the teeth;
28.—a first thread;
29.—a second thread;
30.—a connecting means;
31.—an axis of projections 22 and 23;
32.—a first wing;
33.—a second wing;
34-34—a top view of the improved surgical device for elevating the Schneiderian membrane.

DETAILED DESCRIPTION OF THE INVENTION

With reference now to the drawings, and particularly to FIGS. 1-3B thereof, an improved surgical device for elevating the Schneiderian membrane embodying the principles and concepts of the present invention.

Figure 1:
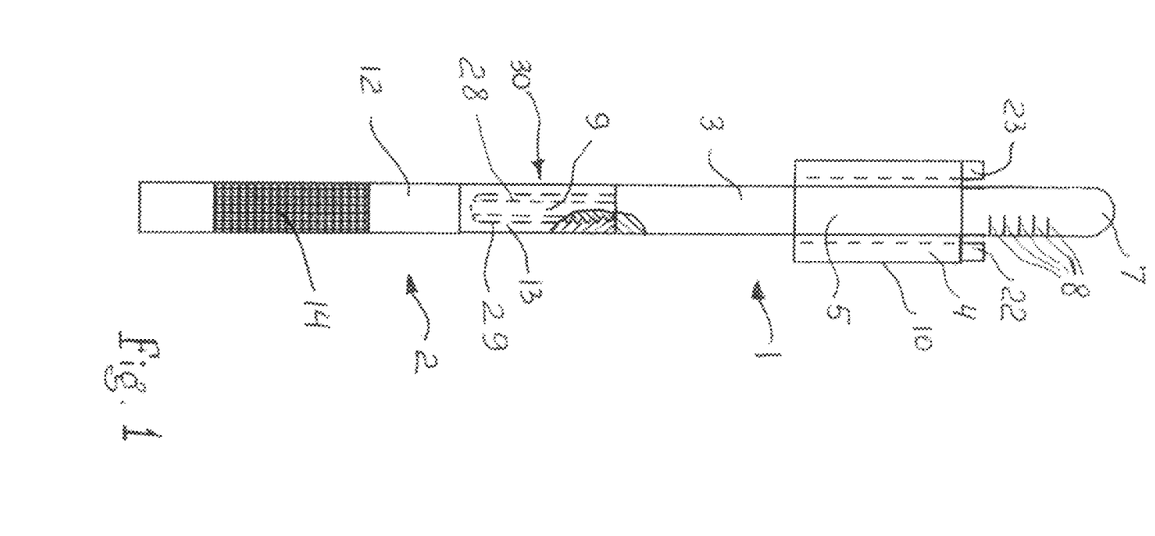
FIG. 1 is a simplified drawing of the improved device.

According to FIG. 1, the surgical device for elevating the Schneiderian membrane includes a main portion 1 and a handle portion 2. The main portion 1 comprises a main means 3 and an adjustment means 4. The main means 3 comprises an adjustment portion 5 and a first connection section 9 (see FIG. 1). The FIG. 1 conditionally depicts the straight configuration of the main means 3.

Figure 2A:
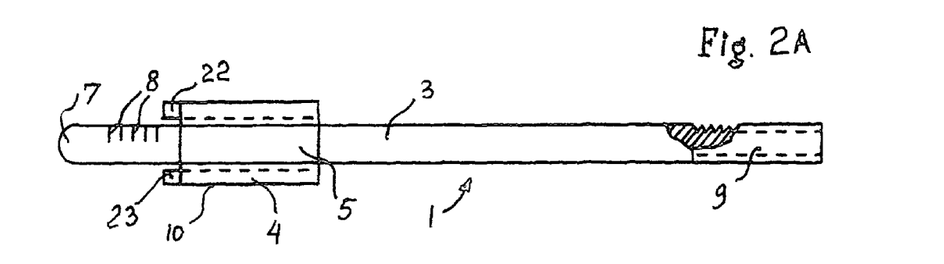
FIG. 2A is a simplified drawing of the main portion of the straight configuration.
Figure 2B:
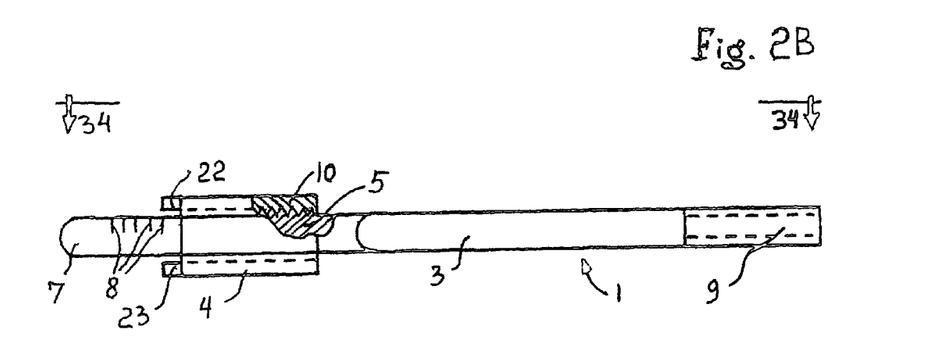
FIG. 2B is a simplified drawing of the main portion of the angled configuration.
Figure 2C:
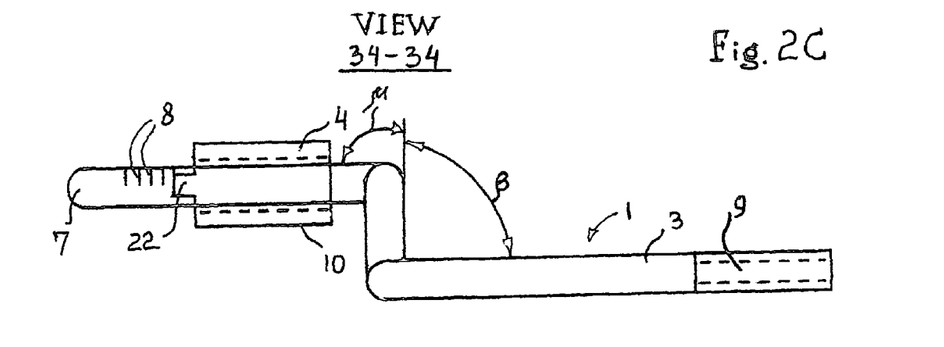
FIG. 2C is a simplified drawing of the top view 34-34 of the angled configuration.

The FIGS. 2A, 2B and 2C illustrate the main portion 1 comprising the main means 3 including also an outer thread 6, a free end 7, and a depth measurement marks 8, The FIG. 2A illustrates the straight configuration of the main means 3 and FIG. 2B illustrates the angled configuration of the main means 3. The top view 34-34 of the angled configuration is shown in FIG. 2C.

Figure 3A:
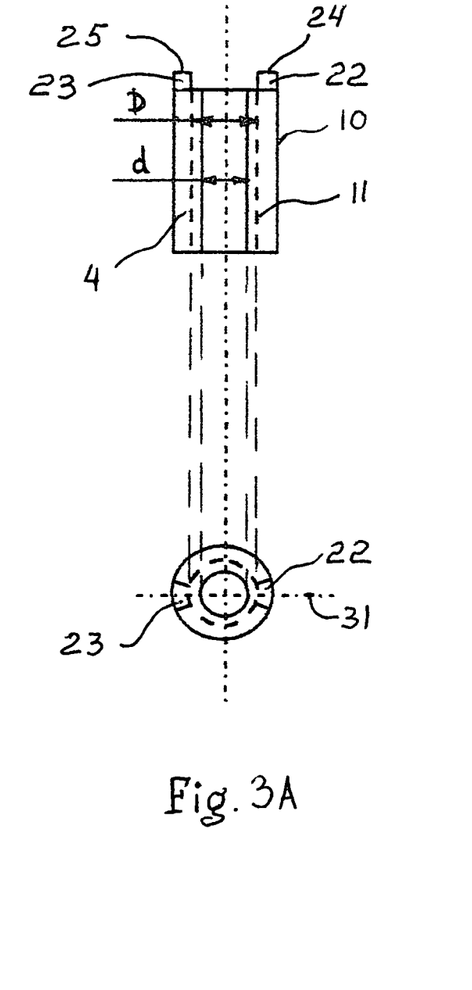
FIG. 3A is a simplified drawing of the adjustment means.

The adjustment means 4 is shown in FIG. 3A and comprises a cylinder 10, an inner thread 11 and a first projection 22 and a second projection 23 (see also FIGS. 1-2C). The projections 22 and 23 are located along axis 31.

The first 22 and second 23 projections can be extended from the cylinder 10 or may be attached (not shown) to the cylinder 10 of the adjustment means 4. The second projection 23 is diametrically opposed from the first projection 22.

Figure 3B:
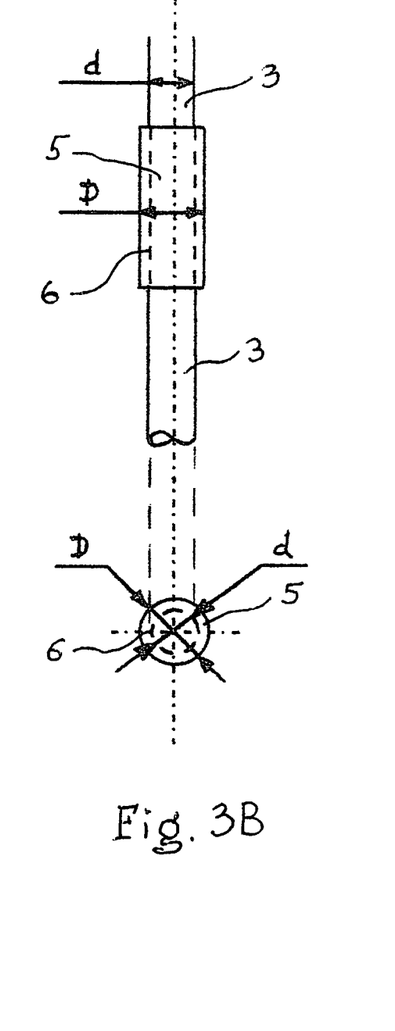
FIG. 3B is a simplified drawing of the adjustment portion of the main means.

Referring FIG. 3B, the adjustment portion 5 includes an outer thread 6 along the adjustment portion 5. The diameter "D" (a first diameter) of the adjustment portion 5 is slightly bigger than the diameter "d" (a second diameter) of the main means 3 of the main portion 1. The difference between the radiuses (not shown) of the adjustment portion 5 and main means 3 is at least slightly bigger than the thickness of the outer thread 6. The main portion 1 may be produced of the different diameters "d", depending on the size of the installing dental implant (not shown), and commonly "d" may be in the range of approximately 2 mm-6 mm (wherein "mm" means millimeters).

The handle portion 2, shown in FIG. 1, includes a handle means 12, a second connection section 13, and a texture 14. The second connection section 13 is located at a first end of said handle portion 2 and the texture 14 is located in an area of a second end of the handle portion 2. The second end of the handle portion 1 is opposite to the first end of said handle portion 1.

The handle means 12 of handle portion 2 may not include the texture 14, but the texture may prevent the dentist's hand sliding along the handle means 12 during procedure of the lifting of the Schneiderian membrane 15, thereby, causing the traumatization or even injury (e.g., puncture, etc.) of the thin membrane 15.

The main means 3 of the main portion 1 may have a straight configuration (FIGS. 1 and 2A) or may be of the angled configuration, as it is shown in FIGS. 2B and 2C (in FIGS. 2B, 2C are shown the front and top projections (views) of the angled main means 3 respectively). The angled main means 3 is designed to aid in the proper positioning of the improved device during the lifting procedure. It should be recognized that the main means 3 of the main portion 1 may be of any geometrical configuration which are not show herein. The angle "β", shown in FIG. 2C (View 34-34), commonly may be in the range of approximately 90°-180°. The angle "μ" (FIG. 2B) commonly may be in the range of 0°-150°. It is understood, that when μ=0° and β=180° the main means 3 has a straight configuration. Also, it is understood that the angled portion of the main means 3 may be bended under the curves (not shown) and not under the "sharp" angles, as it is conventionally shown in FIG. 2B.

As it is shown in FIGS. 1 and 2A, 2B, the main means 3 of the main portion 1 includes a first connection section 9 which is located at another side (a second side) of said main means 3 (the side opposite to the side of location of the free end 7) and coupled with the second connection section 13 of the handle portion 2. In FIGS. 1, 2A, 2B conditionally shown the threaded coupling of the first connection section 9 of the main portion 1 with the second connection section 13 of the handle portion 2 via a first thread 28 and a second thread 29 respectively (FIG. 1), but it may be used any reasonably convenient principles of coupling (for instance, the tighten (friction) coupling (not shown), locking coupling (not shown), etc.). As it is understood from the figures herein, the first connection section 9 (comprising the first thread 28) and the second connection section 13 (comprising the second thread 29) form the connecting means 30.

The main portions 1 of the different diameters "d" are interchangeable to be used for the same handle portion 2. Also, according to FIGS. 1 and 2A, 2B and 2C, the free end 7 is located at the one side (a first side) of said main means 3 and comprises a semispherical configuration, but it may be of any reasonable not sharp configuration. Additionally, the surfaces of the main means 3 and specially of the free end 7 should have the smooth preferably fine (well polished) surfaces in order not to traumatize (injure) the gum 18, walls of the tooth channel (socket) 16, jaw bone 20, and the membrane 15 during its lifting.

The improved device for dental implant installation operates as follows. The improved device provide the preparation for growing of maxillary jaw bone (alveolar bone) in order to obtain adequate volume of osseous structure (e.g., draft material) and the installation of the dental implant in the grown maxillary jaw bone. Preferably, the lifting and lateral separation of the membrane from the sinus compartment floor is accomplished by the use of the improved device.

Figure 4:
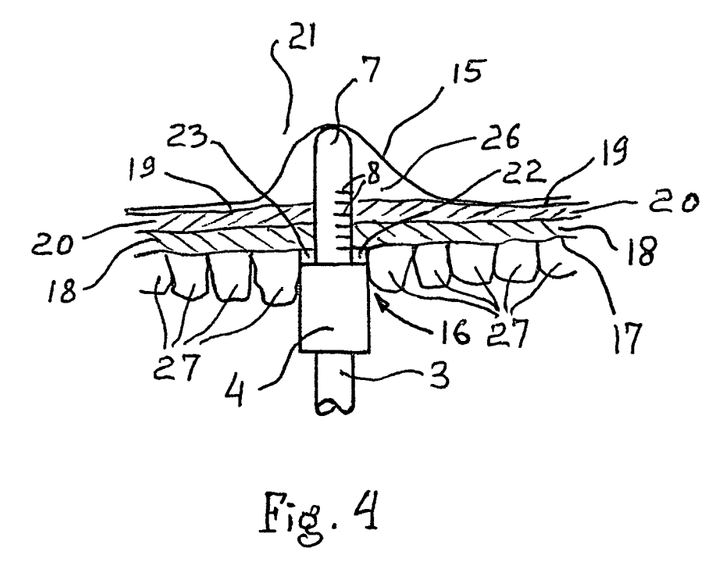
FIG. 4 is a simplified presentation of the elevated Schneiderian membrane.

According to FIG. 4, the free end 7 of the main means 3 of the main portion 1 is initially inserted into the tooth socket 16 in such manner, that the depth of the inserted portion, measured by the depth measurement marks 8, is adequate, for instance, to the length, measured for example via X-ray treatment) from the lower surface 17 of the gum 18 to the upper surface 19 of the bone 20.

The upper surface 19 of the maxillary bone 20 is a floor of the sinus compartment 21 on which the Schneiderian membrane 15 is rested. The adjustment means 4 is initially adjusted in such manner, that the tops 24 and 25 of the projections respectively 22 and 23 are coincide with the depth measurement mark 8, which adequate to the length from the lower surface of the gum to the vertex point of the lifted membrane 15. After these steps, the dentist continue to insert the main means 3 deeper through the socket 16, thereby, laterally lifting the membrane 15 from the floor of the sinus compartment 21 until the projections 22 and 23 will lean (rest) on the gum 18 (the upper surface 19 of the bone 20 is a floor of the sinus compartment 21). The elevated membrane 15 forms the draft material pocket 26 to be filled with the draft material (not shown) after the improved device will be pulled out of the socket 16 and replaced with the draft material filler (not shown). Then the dental implant (not shown) may be installed into the socket (tooth channel) 16 (or may be installed later after the bone draft material and jaw bone will achieve the solid formation). This procedure of the membrane 15 lateral release and elevation is continued until a planned amount of the volume of the pocket 26 will achieve the a priory predetermined size.

In the FIG. 4 is illustrated the insertion of the main means 3 of the main portion 1 of the improved device between the teeth 27, but the improved device may be used when socket 16 is not surrounded by the teeth. In such circumstances the projections 22 and 23 may have another configuration and/or sizes, etc. For instance, the projections 22 and 23 may be of the elongated configuration (FIG. 5) or any other reasonable geometric configuration (not shown) and/or size (not shown). The free end 7 is shown of hemi-spherical configuration, but it may be of any reasonable configuration and size. It should be understood that the term/word "configuration" herein above and bellow means any possible regular or irregular form, shape, etc.

Figure 5:
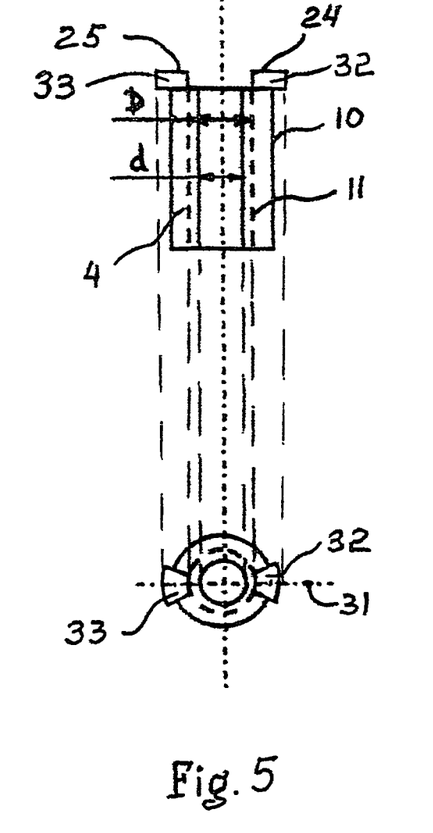
FIG. 5 is a simplified drawing of another variant of the adjustment means.

It should be understood, that the projections 22 and 23 in FIG. 4 are, for example, shown in such position of the adjustment means 4, that the axis 31 (FIG. 3A) of the projections 22 and 23 is coincide with the line of the teeth 27 (the axis 31 is located along the jaw bone 20) and projections 22, 23 rest on the gum 18, but the projections 22 and 23 can rest on the bone 20 (the rest on the bone 20 is not shown). Preferably during dental procedure for the Schneiderian membrane 15 lifting, the tops 24 and 25 respectively of the projections 22 and 23 rest on the jaw bone 20 at the position of the adjustment means 4 when the axis 31 of the projections 22, 23 is approximately perpendicular (not shown) to the jaw bone 20 (the axis 31 is perpendicular [approximately perpendicular] to the line of the teeth 27 [approximately perpendicular {not shown} to the gum 18]), and wherein the bone 20 is in advance temporarily surgically freed of the gum 18 (not shown) in the place (not shown) of the dental surgical procedure for the membrane 15 lifting and dental implant (not shown) installation. As it is mentioned herein above, the projections 22, 23 can be of any reasonable configuration, and, for example, can be of the form of the first and second wings 32, 33 elongated in the direction of the axis 31, as it is shown in FIG. 5. A first wing 32 corresponds to the first projection 22 and a second wing 33 corresponds to the second projection 23. Again, it should be understood, that the wings 32 and 33 can extend from the cylinder 10 of the adjustment means 4 or can be attached (not shown) to the cylinder 10 of the adjustment means 4, and may be of any reasonable configuration/shape (not shown) different to the shape of wings 32, 33 shown in FIG. 5.

It should be also understood that the main portion 1 and handle portion 2 may not be separable/detachable (not shown) and the improved device can be as a one solid entire piece configuration (not as the coupled separate portions [e.g., FIG. 1]). For example, the main portion 1 can extend from the handle portion 2 [not shown], etc.

All components, means may be made of any reasonably safe and hygienic material and preferably of the surgical steel.

Accordingly the reader will see that, according to the invention, I have provided an improved surgical device for elevating the Schneiderian membrane. There has thus been outlined, rather broadly, the more important features of the invention. In this respect, it is understood that the invention is not limited in its application to the details of steps, construction and to the arrangements of the components set forth in the description and/or drawings. The invention is capable of other embodiments and of being practiced and carried out in various ways. Also, it is to be understood that the phraseology and terminology employed herein are for the purpose of description and should not be regarded as limiting.

While the above description contains many specificities, these should not construed as limitations on the scope of the invention, but as exemplification of the presently-preferred embodiments thereof. Many other ramifications are possible within the teaching to the invention. For example, an improved surgical device for elevating the Schneiderian membrane can be successfully used not only for installation of the dental implants in the maxillary jaw bone, but also for installation of the dental implants in the mandibular jaw bone by growing of alveolar bone in order to obtain adequate volume of osseous structure.

As such, those skilled in the art will appreciate that the conception, upon which this disclosure is based, may readily be utilized as a basis for the designing of other structures, for carrying out the several purpose of the present invention. It is important, therefore, that the claims be regarded as including such equivalent constructions insofar as they do not depart from the spirit and scope of the present invention.

What is claimed is:

1. A surgical device for elevating the Schneiderian membrane, comprising:
 a main portion of said surgical device for said elevating of said Schneiderian membrane, including:
  a main element having a bended configuration along an unthreaded portion of the main element, wherein said main element comprises:
   an adjustment portion including an outer thread along said adjustment portion, wherein a diameter of said adjustment portion is bigger than a diameter of said main element of said main portion;
   a free end located at a first side of said main element;
   a set of depth measurement marks located in an area of said free end;
   a first connection section located at a second side of said main element, wherein a bended portion of said bended configuration of said main element has an angle in a range of 90°-180° with respect to the longitudinal axis of the main element at a first bended location located in an area of said main element between said outer thread and said first connection section, and the bended portion has an angle in the range of 0°-150° with respect to the longitudinal axis of the main element at a second bended location located in an area of said main element between said outer thread and said first bended location;
  an adjustment element, comprising:
   a cylinder located between the second bended location and the set of depth measurement marks, the cylinder including an inner thread along said cylinder, wherein said inner thread is coupled with said outer thread of said adjustment portion of said main element;
   a first projection extended from said cylinder;
   a second projection extended from said cylinder and diametrically opposed from said first projection, wherein said first and second projections each have a longitudinal axis parallel to a longitudinal axis of the cylinder, and said first and second projections are configured to rest on a lower surface of a patient's gum;
 a handle portion of said surgical device for said elevating of said Schneiderian membrane including a handle element comprising a second connection section located at a first end of said handle portion, wherein said second connection section is coupled with said first connection section of said main element of said main portion by a threaded coupling, and wherein said handle portion includes a texture on an outer surface of said handle element of said handle portion, and wherein said texture is located in an area of a second end of said handle portion, and wherein said second end of said handle portion is located opposite to said first end of said handle portion.

* * * * *